United States Patent
Tsukuda et al.

(10) Patent No.: US 6,247,350 B1
(45) Date of Patent: Jun. 19, 2001

(54) SENSOR

(75) Inventors: Hiroshi Tsukuda, Shiga; Chaki Okumura, Ibaraki, both of (JP)

(73) Assignee: Daikin Industries Limited, Osaka (JP)

( * ) Notice: Subject to any disclaimer, the term of this patent is extended or adjusted under 35 U.S.C. 154(b) by 0 days.

(21) Appl. No.: 09/403,587

(22) PCT Filed: Apr. 23, 1998

(86) PCT No.: PCT/JP98/01891

§ 371 Date: Feb. 25, 2000

§ 102(e) Date: Feb. 25, 2000

(87) PCT Pub. No.: WO98/48266

PCT Pub. Date: Oct. 29, 1998

(30) Foreign Application Priority Data

Apr. 24, 1997 (JP) .................................................. 9-107949

(51) Int. Cl.[7] .......................... G01N 27/46; G01N 27/30; G01N 27/12
(52) U.S. Cl. ........................ 73/31.05; 73/19.1; 73/31.05; 73/61.41; 422/82.04; 422/82.02
(58) Field of Search ................................. 73/31.05, 19.1, 73/19.01, 23.32, 61.41; 422/82.02–82.04

(56) References Cited

U.S. PATENT DOCUMENTS

| | | | |
|---|---|---|---|
| 4,241,019 | * 12/1980 | Nakatani et al. | 422/94 |
| 4,413,502 | * 11/1983 | Ohta et al. | 73/23 |
| 4,450,428 | * 5/1984 | Ohta et al. | 338/34 |
| 4,660,407 | * 4/1987 | Takami et al. | 73/23 |
| 5,233,860 | * 8/1993 | Mori et al. | 73/1 G |
| 5,421,189 | * 6/1995 | Dussault | 73/19.1 |
| 5,565,085 | * 10/1996 | Ikeda et al. | 205/777.5 |
| 5,777,207 | * 7/1998 | Yun et al. | 73/31.05 |
| 5,777,208 | * 7/1998 | Martell et al. | 73/31.06 |
| 5,987,965 | * 11/1999 | Martell et al. | 73/31.06 |
| 6,082,175 | * 7/2000 | Yoshikawa et al. | 73/23.31 |

* cited by examiner

Primary Examiner—Hezron Williams
Assistant Examiner—David J. Wiggins
(74) Attorney, Agent, or Firm—Smith, Gambrell & Russell, LLP

(57) ABSTRACT

A sensor such as for sensing dissolved oxygen in plural cells spaced apart from each other by a predetermined distance includes projection sections provided at intervals spaced according to the predetermined distance on an edge section of a plate shape base body. At least an active electrode and a counter-electrode are at predetermined positions on each projection section, and lead-out terminals are provided at predetermined positions on the substrate facing the substrate portion where the projection sections are formed. The substrate has wiring electrically connecting both the active electrodes and the counter-electrode to the lead-out terminals. This arrangement greatly reduces measurement labor and variance in measurement data results. In addition, it increases the number of objects that can be measured during a measurement operation.

8 Claims, 15 Drawing Sheets

SENSOR

TECHNICAL FIELD

The present invention relates to a sensor. More particularly, the present invention relates to a sensor which is suitable for performing measurement of objects (for example, test solution) using a micro-plate which has object housing chambers of multiple lines and multiple columns.

BACKGROUND ART

From the past, a micro-plate (a micro-plate for a high throughput system) is supplied which has object housing chambers (cells) of multiple lines and multiple columns. The micro-plate determined its specification in size, number of cells, pitch between cells and the like. The micro-plate is popularly supplied which has cells of 8-lines and 12-columns.

When a dissolved oxygen amount is to be measured, for example, a sensor is employed in the past which is arranged as a single sensor. That is, the sensor arranged as a single sensor is intruded in one cell so that the sensor is contacted to the object which is housed within the cell and that an electrical signal is output therefrom which represents a measurement result.

When the above measurement is carried out, the sensor or multiple sensors should be contacted to the object by intruding the sensor arranged as a single sensor into each cell sequentially, or by intruding multiple sensors each being arranged as a single sensor into corresponding cells, so that disadvantages arise in that much labor is required for the measurement and that dispersion is generated in measerement data. Further, a disadvantage arises in that a number of objects is limited which can be measured at one measuring operation, because of spatial limitation and limitation in measurement labor.

The present invention was made in view of the above problems.

It is an object of the present invention to offer a sensor which can greatly reduce measurement labor, can greatly reduce dispersion in measurement data, and can lighten the limitation in the number of objects which can be measured at one measuring operation.

DISCLOSURE OF INVENTION

A sensor according to the present invention disposes multiple electrode sections spaced at intervals according to each of an every predetermined distance, each electrode section having at least an active electrode and a counter-electrode, unites the all electrode sections and multiple lead-out terminals which output measurement signals of each electrode section.

A sensor according to the present invention comprises a base body having a plate shape, projection sections provided at an outer predetermined position at every predetermined distance, at least active electrodes and counter-electrodes provided at a predetermined position of each projection section, and multiple lead-out terminal for outputting measurement signals of each electrode section, the lead-out terminal being provided at a predetermined position of the base body which position opposes to a portion at which the projection section is provided.

A sensor according to the present invention further comprises a connector which is connected to the lead-out terminals in a removable manner and an amplifier which amplifies the measurement signals output through the lead-out terminals, wherein the connector and the amplifier are united in one body.

A sensor according to the present invention employs a connector which connects multiple base bodies in parallel to one another and in a removable manner, and employs an amplifier which amplifies measurement signals, respectively, each measurement signal being output through the corresponding lead-out terminal.

A sensor according to the present invention comprises multiple object housing chambers, and wherein electrode sections each having at least an active electrode and a counter-electrode are formed at a bottom section of each object housing chamber, and multiple lead-out terminals for outputting measurement signals of each electrode section are united to the object housing chambers.

A sensor according to the present invention comprises a base body having a plate shape, projection sections of multiple lines and multiple columns, each projection section being projected by a predetermined angle with respect to one surface of the base body, electrode sections each including at least an active electrode and a counter-electrode which electrode section is provided at a predetermined position of each projection section, and multiple lead-out terminals for outputting measurement signals of each electrode section which lead-out terminals are provided at predetermined positions on an edge section of the base body.

A sensor according to the present invention comprises multiple object housing chambers, and wherein multiple electrode sections each having at least an active electrode and a counter-electrode are formed on a bottom inner face of each object housing chamber, and multiple lead-out terminals for outputting measurement signals of each electrode section, each lead-out terminal being provided so that the lead-out terminal is exposed at an outer face of a bottom section of each object housing chamber.

A sensor according to the present invention comprises multiple object housing chambers, multiple inner projections each projecting to inner side from a center section of an inner face of an edge section of each object housing chamber, multiple electrode sections each having at least an active electrode and a counter-electrode, each electrode section being formed at a predetermined position of outer face of the inner projection and/or the inner face of the edge section, and multiple lead-out terminals for outputting measurement signals of each electrode section, each lead-out terminal being provided so that the lead-out terminal is exposed at an outer face of a bottom section of each object housing chamber.

A sensor according to the present invention employs an axial section as the inner projection which axial section extends upwards from a central section of the bottom inner face of each object housing chamber, and employs an electrode section which has an active electrode on an outer face of the axial section and a counter-electrode on an upper face of the bottom section.

When the sensor according to the present invention is employed, multiple electrode sections and multiple lead-out terminals can be handled in one body, labor for measurement is greatly reduced and dispersion in measurement data is greatly reduced, a spatial limitation and limitation in measurement labor are greatly reduced, and, limitation in a number of objects which can be measured at one measurement operation is lightened, because the sensor disposes multiple electrode sections at every predetermined distance, each electrode section having at least an active electrode and a counter-electrode, unites the all electrode sections and multiple lead-out terminals which output measurement signals of each electrode section.

When the sensor according to the present invention is employed, an operation and effects can be realized which are similar to those discussed, because the sensor comprises a base body having a plate shape, projection sections provided at an outer predetermined position at every predetermined distance, at least an active electrode and a counter-electrode provided at a predetermined position of each projection section, and multiple lead-out terminals for outputting measurement signals of each electrode section, the lead-out terminal being provided at a predetermined position of the base body which position opposes to a portion at which the projection section is provided.

When the sensor according to the present invention is employed, the measurement signals which are low in their level are immediately amplified so that noise resistance is improved, and an operation and effects can be realized which are similar to those discussed, because the sensor further comprises a connector which is connected to the lead-out terminals in a removable manner and an amplifier which amplifies the measurement signals output through the lead-out terminals, wherein the connector and the amplifier are united in one body.

When the sensor according to the present invention is employed, limitation in a number of objects which can be measured at one measurement operation is further lightened, and, an operation and effects can be realized which are similar to those discussed, because the sensor employs a connector which connects multiple base bodies in parallel to one another and in a removable manner, and employs an amplifier which amplifies measurement signals, respectively, each measurement signal being output through the corresponding lead-out terminal.

When the sensor according to the present invention is employed, multiple electrode sections and multiple lead-out terminals can be handled in one body, and, an operation and effects can be realized which are similar to those discussed, because the sensor comprises multiple object housing chambers, and wherein multiple electrode sections each having at least an active electrode and a counter-electrode is formed at a bottom section of each object housing chamber, and multiple lead-out terminals for outputting measurement signals of each electrode section are united to the object housing chambers.

When the sensor according to the present invention is employed, measurement labor is more greatly reduced, and, an operation and effects can be realized which are similar to those discussed, because the sensor comprises a base body having a plate shape, projection sections of multiple lines and multiple columns, each projection section being projected by a predetermined angle with respect to one surface of the base body, multiple electrode section each including at least an active electrode and a counter-electrode which electrode section is provided at a predetermined position of each projection section, and multiple lead-out terminals for outputting measurement signals of each electrode section which lead-out terminals are provided at predetermined positions on an edge section of the base body.

When the sensor according to the present invention is employed, multiple electrode sections and multiple lead-out terminals can be handled in one body so that labor for measurement is greatly reduced and dispersion in measurement data is greatly reduced, and, though a plurality of electrode sections are disposed at every predetermined distance, a spatial limitation and limitation in measurement labor are greatly reduced so that limitation in a number of objects which can be measured at one measurement operation is lightened, because the sensor comprises multiple object housing chambers, and wherein multiple electrode sections each having at least an active electrode and a counter-electrode are formed on a bottom inner face of each object housing chamber, and multiple lead-out terminals for outputting measurement signals of each electrode section, each lead-out terminal being provided so that the lead-out terminal is exposed at an outer face of a bottom section of each object housing chamber.

When the sensor according to the present invention is employed, multiple electrode sections and multiple lead-out terminals can be handled in one body so that labor for measurement is greatly reduced and dispersion in measurement data is greatly reduced, and, though multiple electrode sections are disposed at every predetermined distance, a spatial limitation and limitation in measurement labor are greatly reduced so that limitation in a number of objects which can be measured at one measurement operation is lightened, and, an area of the active electrode and an area of the counter-electrode are easily increased without changing the inner diameter of the object housing chamber, because the sensor comprises multiple object housing chambers, multiple inner projections each projecting to inner side from a center section of an inner face of an edge section of each object housing chamber, multiple electrode sections each having at least an active electrode and a counter-electrode, each electrode section being formed at a predetermined position of outer face of the inner projection and/or the inner face of the edge section, and multiple lead-out terminals for outputting measurement signals of each electrode section, each lead-out terminal being provided so that the lead-out terminal is exposed at an outer face of a bottom section of each object housing chamber.

When the sensor according to the present invention is employed, an operation and effects can be realized which are similar to those discussed, because the sensor employs an axial section as the inner projection which axial section extends upperwards from a central section of the bottom inner face of each object housing chamber, and employs an electrode section which has an active electrode on an outer face of the axial section and a counter-electrode on an upper face of the bottom section.

BEST MODE FOR CARRYING OUT THE INVENTION

Hereinafter, referring to the attached drawings, we explain a sensor of embodiments according to the present invention in detail.

Figure 1:
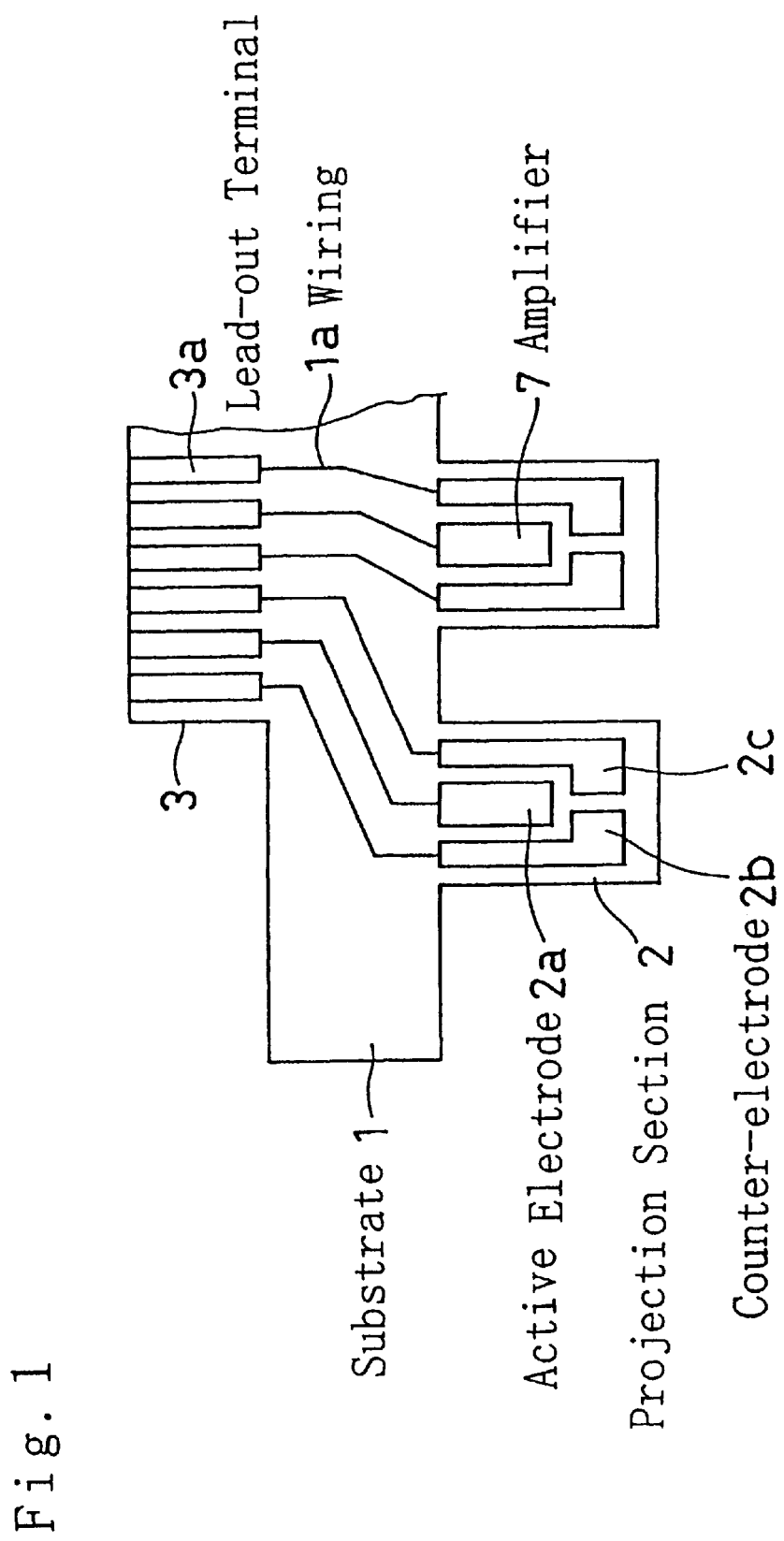
FIG. 1 is a front view illustrating a sensor of an embodiment according to the present invention.

FIG. 1 is a front view illustrating a sensor of an embodiment according to the present invention.

The sensor comprises an insulation substrate 1 having a square shape in its entirety, first projection sections 2 formed at every predetermined distance on one longer edge of the insulation substrate 1, and a second projection section 3 on the other longer edge of the insulation substrate 1, the second projection section 3 having a predetermined width. And, an active electrode 2a, a counter-electrode 2b and a reference electrode 2c are formed on a surface of each first projection section 2, the active electrode 2a, the counter-electrode 2b and the reference electrode 2c consist an electrode section. Further, multiple lead-out terminals 3a are formed on a surface of the second projection section 3 spaced at intervals according to each of an every predetermined distance. And, multiple wirings 1a are formed so that each active electrode 2a, each counter-electrode 2b and each reference electrode 2c are connected to corresponding lead-out terminals 3a through corresponding wirings 1a. It is preferable that the active electrodes 2a, the counter-electrodes 2b, the reference electrodes 2c, the lead-out terminals 3a and the wirings 1a are formed using printing technique. Further, the sensor having the above arrangement may be a sensor which detects a dissolved oxygen amount within an object, or may be a sensor which detects hydrogen peroxide.

Figure 2:
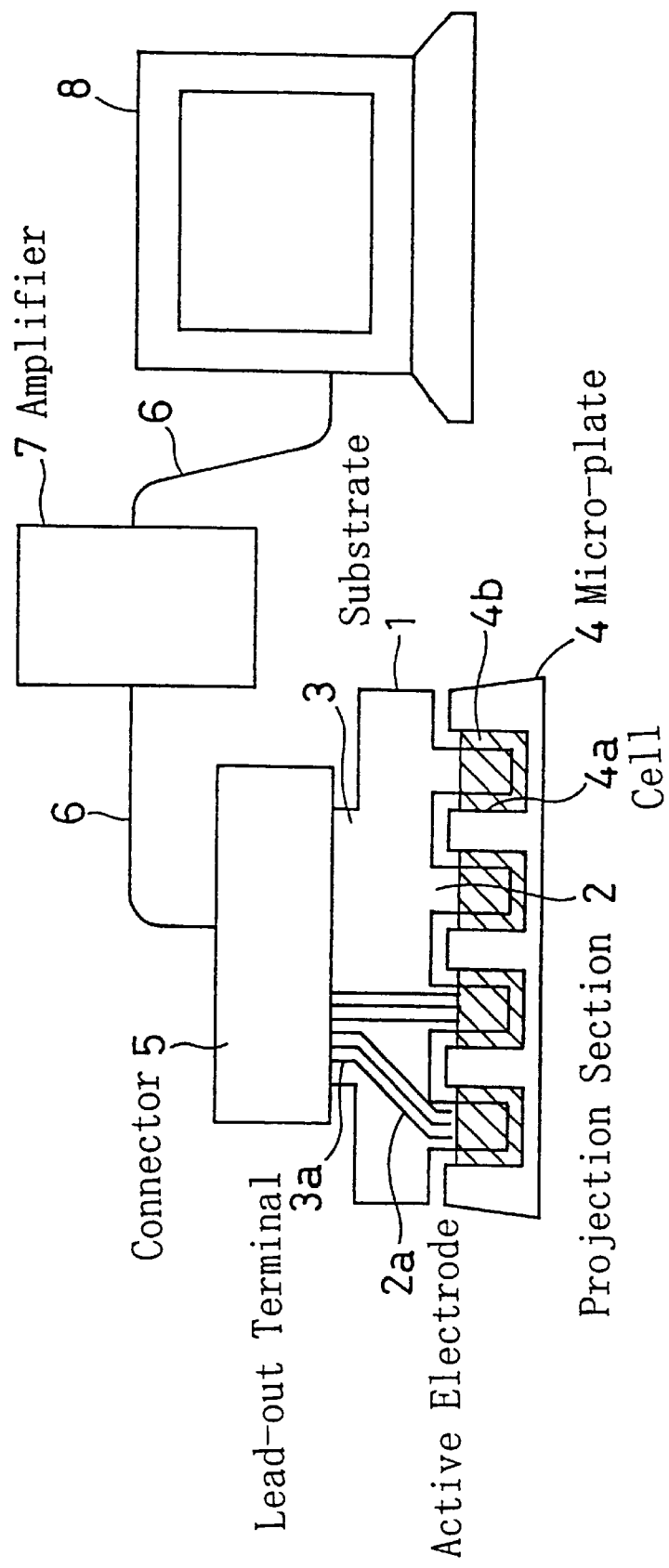
FIG. 2 is a schematic view illustrating a condition for measuring objects using the sensor having the arrangement illustrated in FIG. 1.

FIG. 2 is a schematic diagram illustrating a measurement condition for measuring objects using the sensor having the arrangement illustrated in FIG. 1.

In FIG. 2, reference numeral 4 represents a micro-plate. Cells 4a are formed at every predetermined distance in the micro-plate 4, and objects 4b are housed within the cells 4a, respectively. And, the first projection sections 2 of the sensor having the arrangement illustrated in FIG. 1 are intruded into corresponding cells 4a so that the electrode section and the object are contacted to one another. The lead-out terminals 3a on the second projection section 3 of the sensor are connected to a connector 5, and the connector 5 is connected to a signal processing apparatus 8 such as a computer through an electric wire 6 and an amplifier 7. Further, an end-point method, a rate method which are known from the past may be employed as a signal processing method.

As is apparent from FIG. 2, a plurality of electrode sections can be intruded within corresponding cells 4a by one handling operation. Also, a plurality of lead-out terminals 3a can be connected to the connector 5 by one handling operation. Therefore, entire labor for measurement is greatly reduced. Further, the first projection sections 2 are determined their distances so that each first projection section 2 corresponds to each cell 4a. Therefore, spatial limitation and limitation in measurement labor are greatly reduced. Further, limitation in a number of objects which can be measured at one measurement operation is lightened. Furthermore, contacting condition of all electrode sections and objects, temperature circumstance, and connecting condition of all lead-out terminals 3a and the connector 5 are made to be almost equal to one another so that dispersion in measurement data is greatly reduced.

Figure 3:
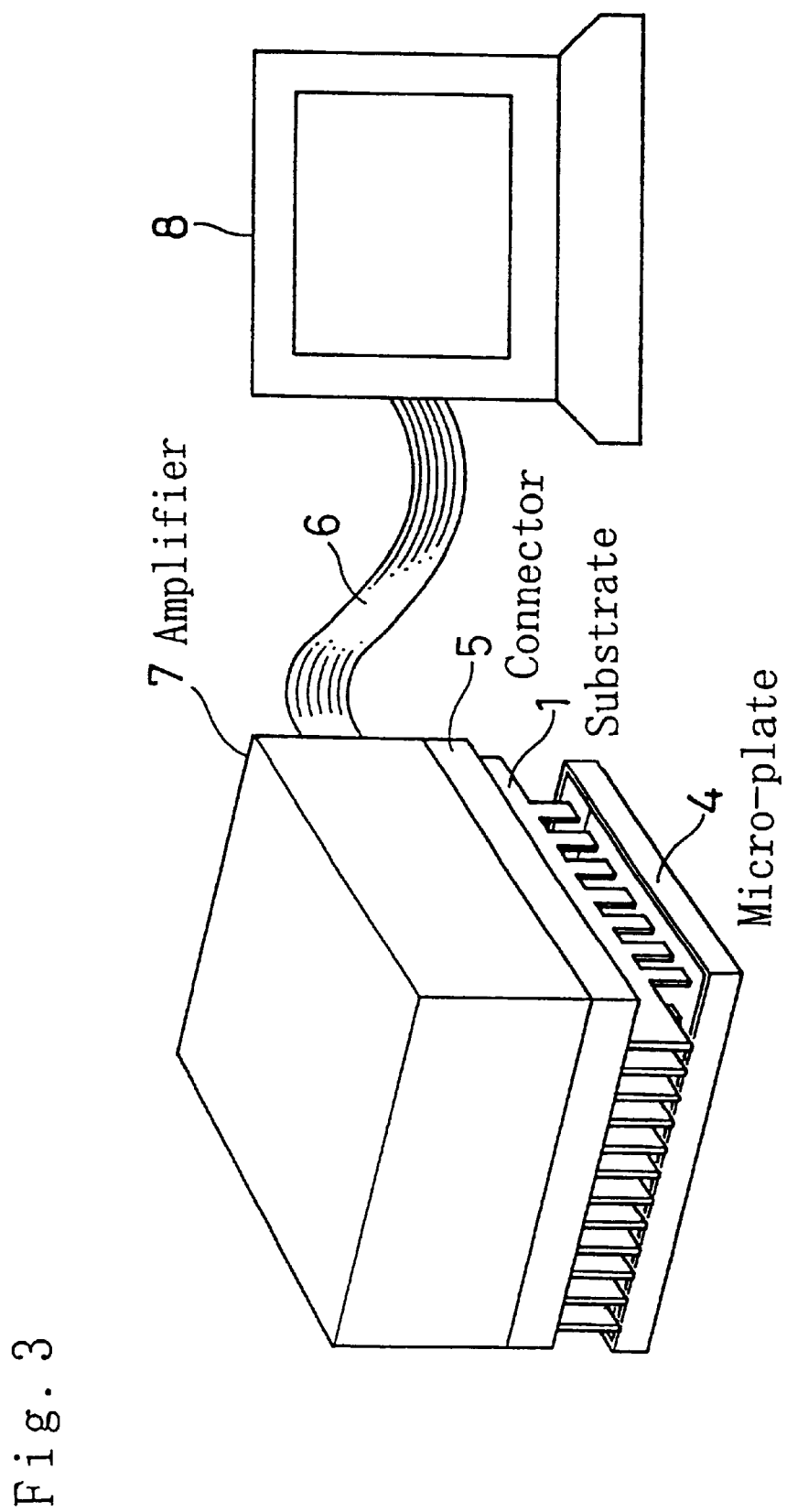
FIG. 3 is a schematic view illustrating a condition for measuring objects using the sensor having the arrangement illustrated in FIG. 1.
Figure 4:
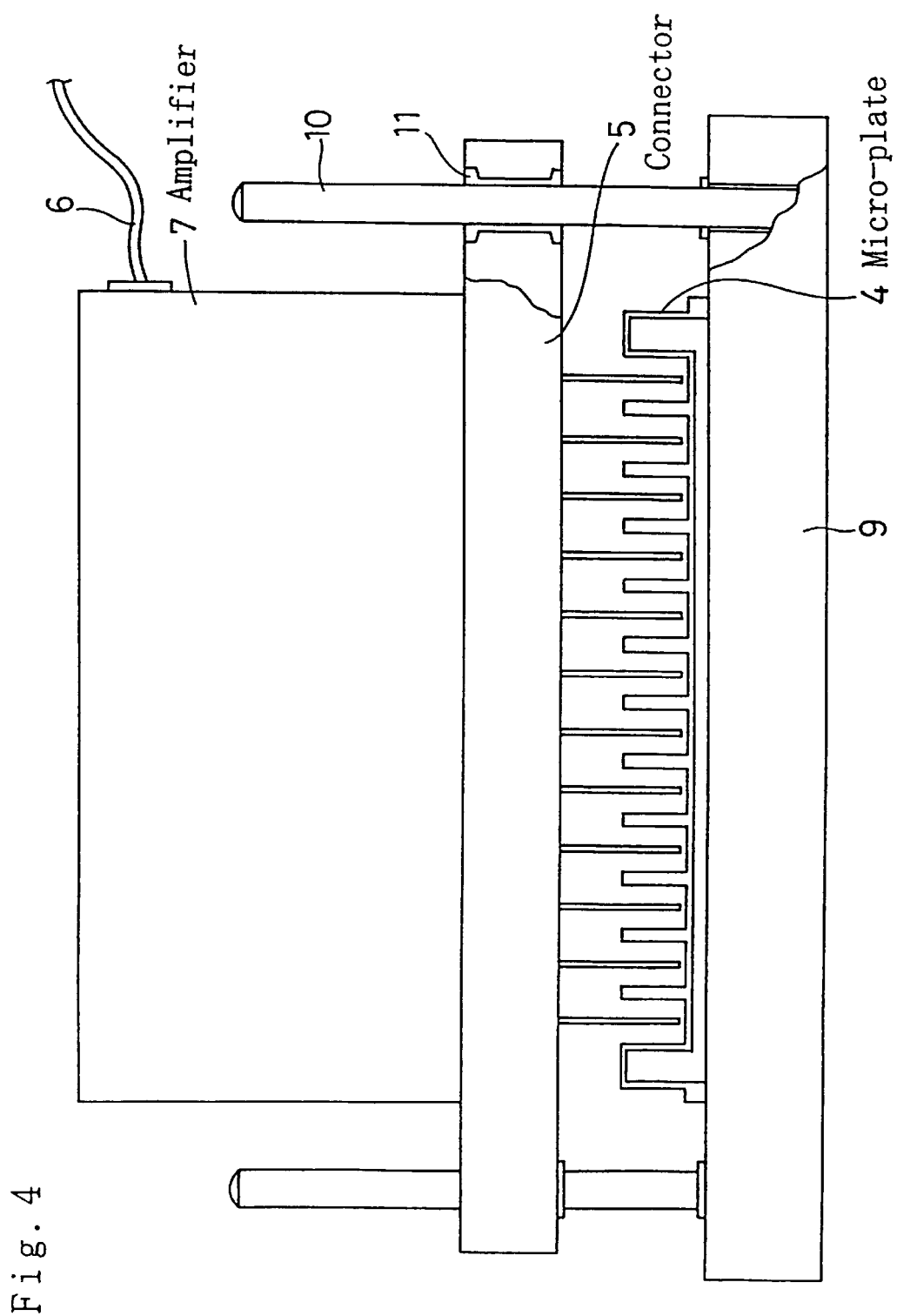
FIG. 4 is a schematic vertical cross-sectional view illustrating a modified example of FIG. 3.

FIG. 3 is a schematic diagram illustrating a measurement condition for measuring objects using the sensor having the arrangement illustrated in FIG. 1.

The measurement condition in FIG. 3 is different from the measurement condition in FIG. 2 in that the measurement condition in FIG. 3 employs a connector 5 which is connected to multiple sensors each having the arrangement illustrated in FIG. 1, the sensors being in parallel to one another, and the connector 5 holding multiple sensors, and that an amplifier 7 is provided to the connector 5 in one body. Arrangement of other sections are the same to those of FIG. 2.

When the measurement condition illustrated in FIG. 3 is employed, a number of objects which can be measured at one measurement operation is greatly increased similarly to FIG. 2. Further, the measurement signals output from the sensor through the lead-out terminals 3a and the connector 5 are supplied to the amplifier 7 immediately under the measurement condition illustrated in FIG. 3, therefore, effects of noises to the measurement signals which are prior to amplification, are greatly reduced in comparison to the measurement condition illustrated in FIG. 2 so that measurement accuracy is greatly improved. Furthermore, operations and effects are realized which are similar to those of FIG. 2.

Figure 17:
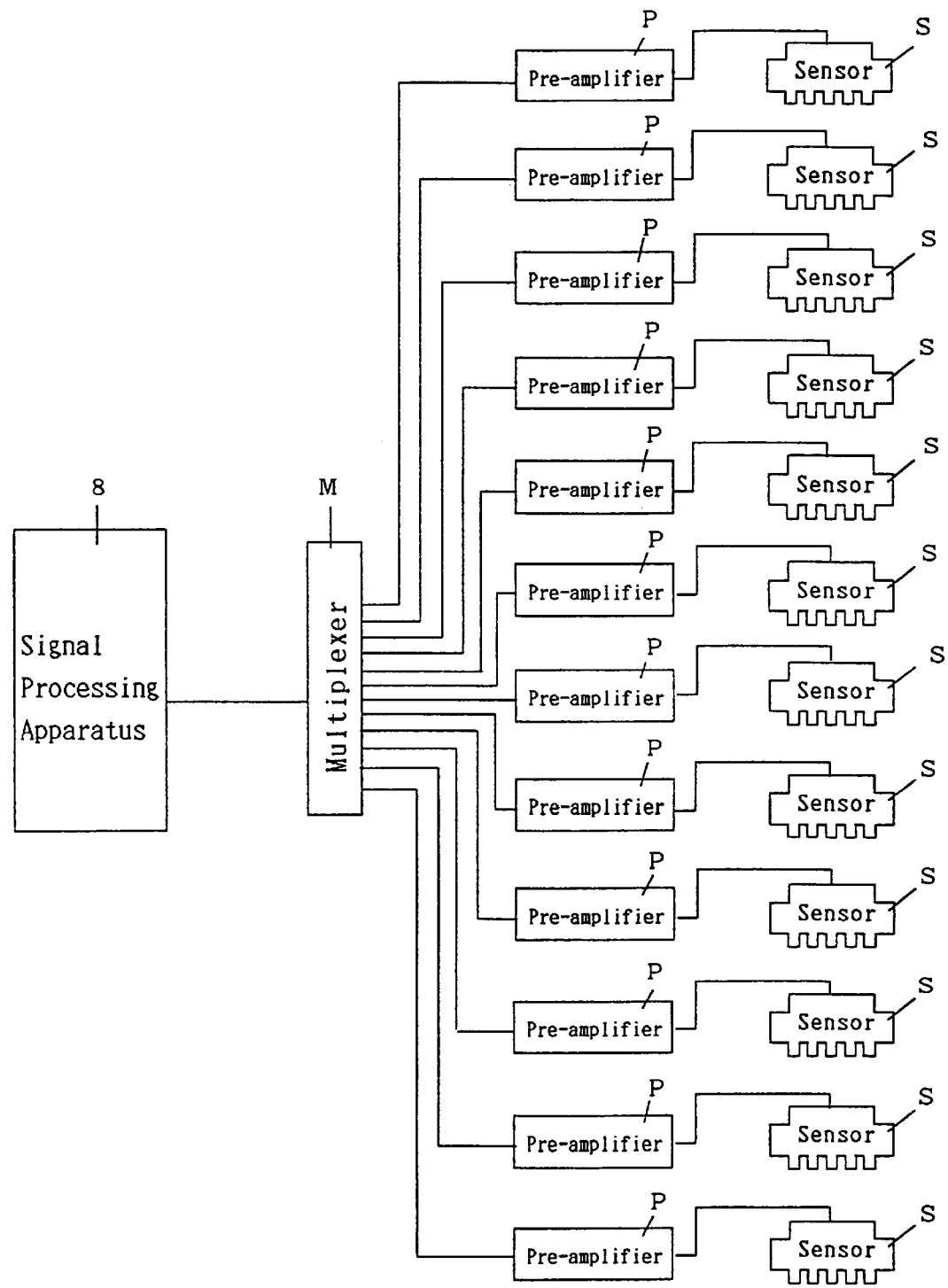
FIG. 17 is a block diagram illustrating an electrical arrangement corresponding to FIG. 3.

FIG. 17 is a block diagram illustrating an electrical arrangement corresponding to this embodiment.

Measurement signals output from a plurality of sensors S are amplified by corresponding pre-amplifier P, and the amplified measurement signals are selectively supplied to a signal processing apparatus 8 through a multiplexer M, respectively.

The signal transmission between the multiplexer M and the signal processing apparatus 8 can be performed using a wiring, or can be performed by communication using RS232C protocol interface. Further, smoothing processing or the like may be performed within the signal processing apparatus 8 for a counterplan against noises, but similar processing may be performed within each pre-amplifier P by incorporating a micro-computer to each preamplifier P.

When the measurement condition illustrated in FIG. 3 is to be employed, and when guide rails 10 are provided at edge sections of a table 9, the table 9 positioning and supporting a micro-plate 4, and when engaging sections 11 for engaging the guide rails 10 are provided at edge sections of the connector 5, the first projection sections 2 can be intruded within corresponding cells 4a by only pressing the connector 5 downwards so that handling operability is improved.

Figure 5:
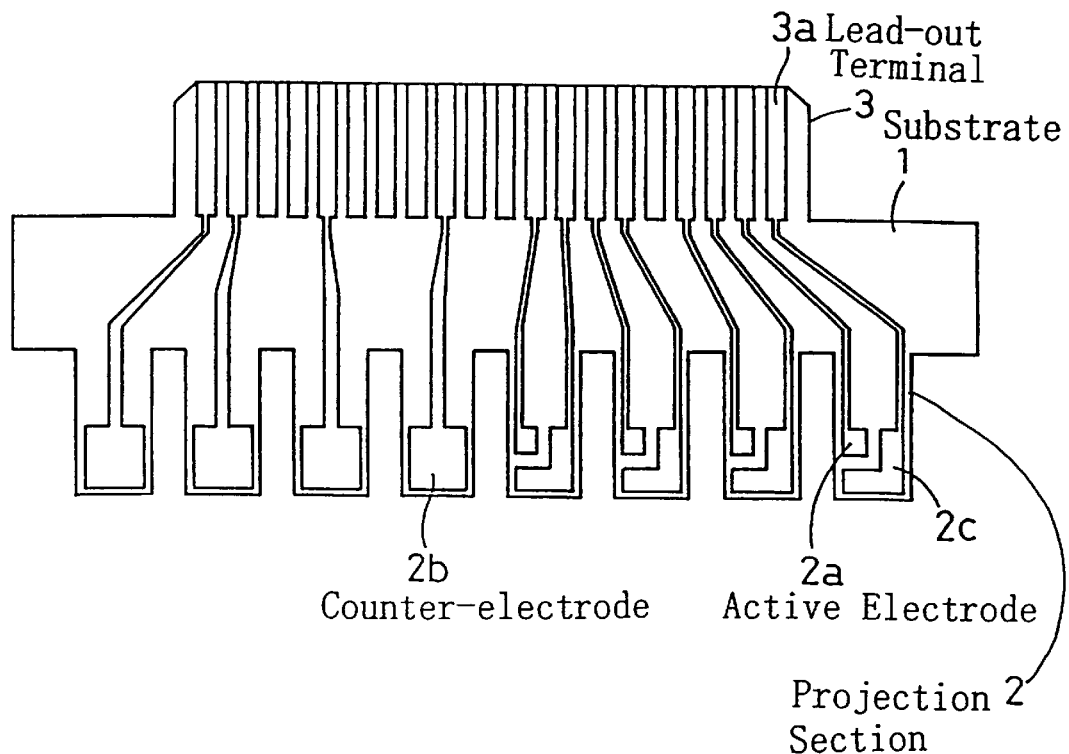
FIG. 5 is a diagram illustrating a sensor of another embodiment according to the present invention.

FIG. 5 is a diagram illustrating a sensor of another embodiment according to the present invention. In FIG. 5, a right half portion represents a front view, while a left half portion represents a rear view.

In the sensor illustrated in FIG. 5, active electrodes 2a and reference electrodes 2c are formed on a front side surface of each first projection section 2, and counter-electrodes 2b are formed on a rear side surface of each first projection section 2. Therefore, an area of the active electrode 2a can be increased in comparison to the sensor illustrated in FIG. 1, the area giving the greatest affect to the measurement signal intensity, so that a measurement sensitivity is improved. Further, operations and effects are realized which are similar to those of FIG. 1.

Figure 6:
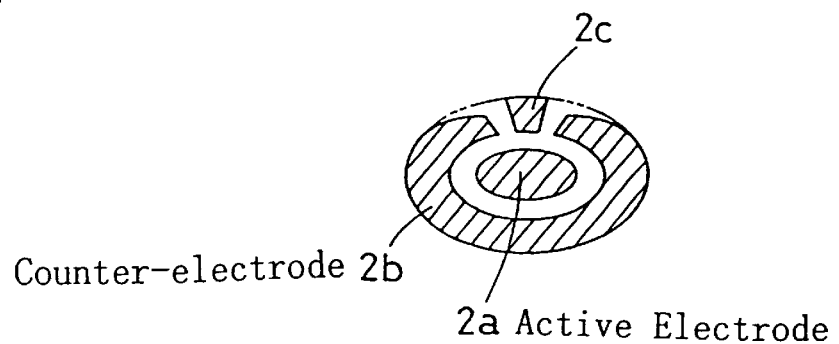
FIG. 6 is a schematic perspective view illustrating a main section of a sensor of further embodiment according to the present invention.

FIG. 6 is a schematic perspective view illustrating a main section of a sensor of a further embodiment according to the present invention.

FIG. 6 illustrates a bottom face of one cell of a micro-plate. The bottom face has an active electrode 2a at the central section, a counter-electrode 2b which surrounds almost entire extent of the active electrode 2a, and a reference electrode 2c at a portion where the counter-electrode 2b does not exist. Further, lead-out terminals and wirings are not illustrated, but they may be formed in the micro-plate in an embedded manner, or they may be formed on a surface of the micro-plate.

When the embodiment illustrated in FIG. 6 is employed, measurement can be carried out by connecting the micro-plate to a signal processing section through a connector, amplifiers and wirings and by supplying objects to each cell 4a under this condition using a pipette for micro-plate or the like. Therefore, measurement labor is greatly reduced. Further, dispersion in measurement data is greatly reduced, because the intruding operation of the electrode section into the cell is not necessary. Also, spatial limitation and limitation in handling operation are determined to be almost zero so that limitation in a number of objects which can be measured at one measurement operation is determined only by a number of cells of the micro-plate.

Figure 7:
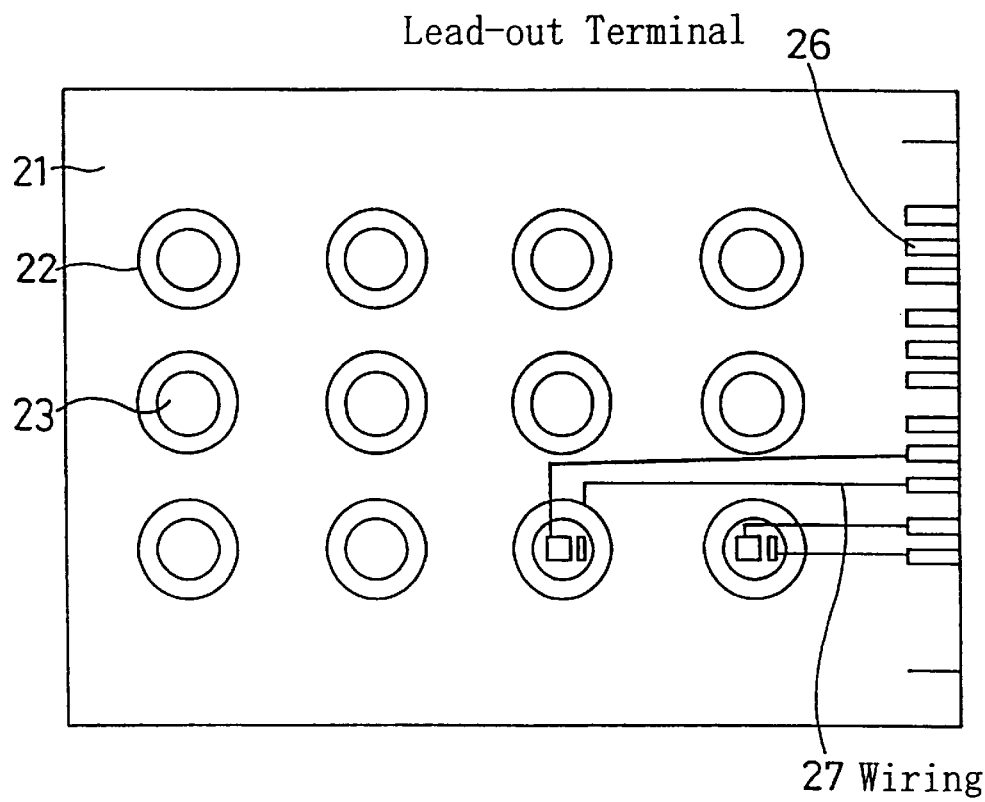
FIG. 7 is a plan view illustrating a sensor of a yet embodiment according to the present invention.
Figure 8:
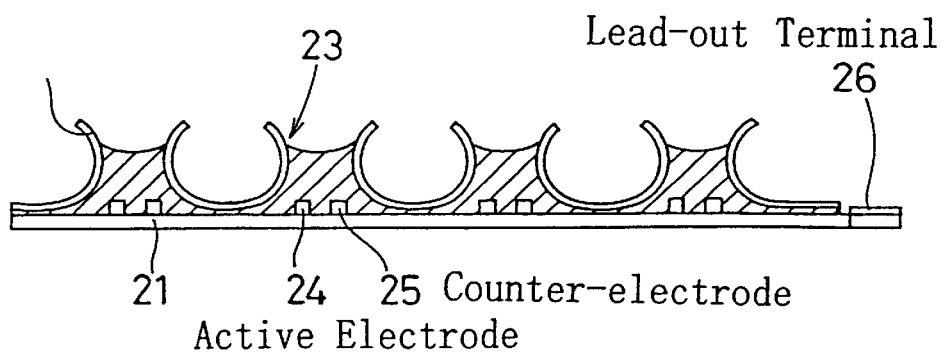
FIG. 8 is a central vertical cross-sectional view of the sensor illustrated in FIG. 7.

FIG. 7 is a plan view of a sensor of yet another embodiment according to the present invention, while FIG. 8 is a central vertical cross-sectional view thereof.

This sensor is arranged by forming multiple cells 23 and by forming active electrodes 24 and counter-electrodes 25 on bottom faces of each cell 23, the cells 23 being formed by fixing partitioning wall members 22 using binder or the like on an upper face of an insulation substrate 21. Further, lead-out terminals 26 are formed on one edge section of the insulation substrate 21, and wirings 27 are formed on the insulation substrate 21, the wirings 27 electrically connecting the active electrodes 24 and counter-electrodes 25 to the lead-out terminals 26.

When this embodiment is employed, operations and effects are realized which are similar to those of the embodiment illustrated in FIG. 6.

Figure 9:
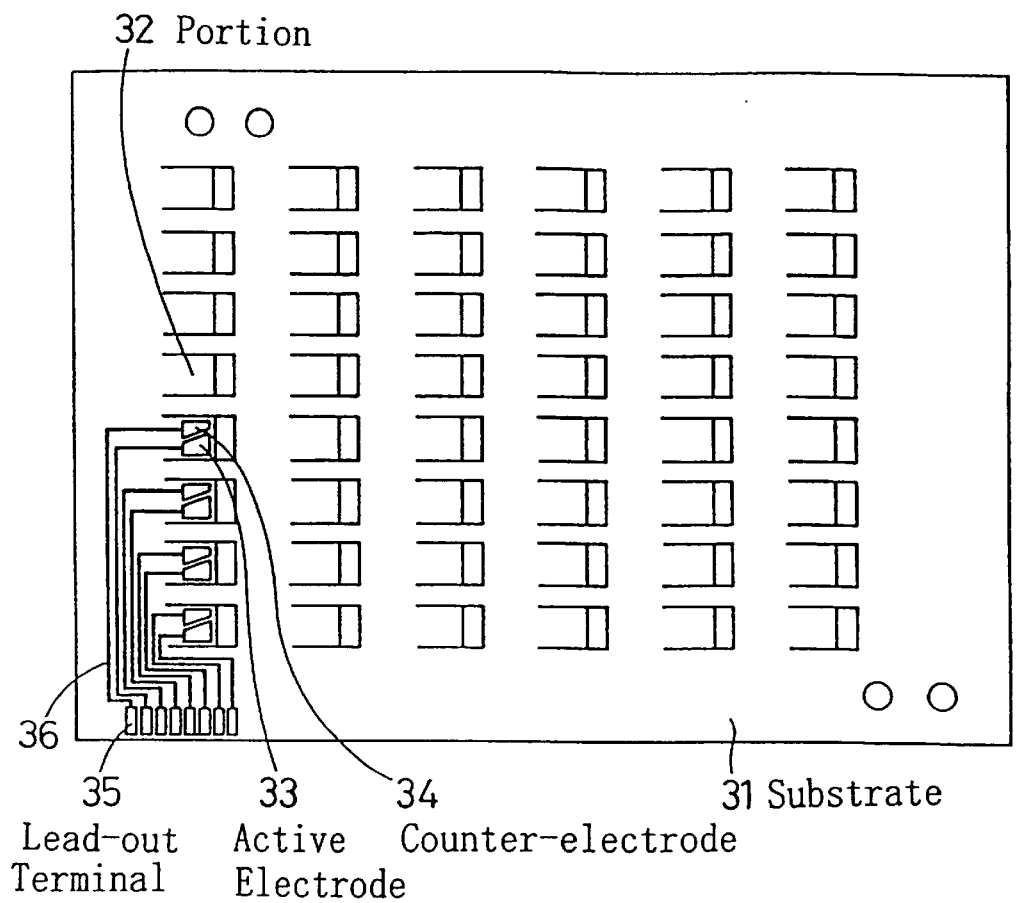
FIG. 9 is a plan view illustrating a sensor of yet another embodiment according to the present invention.
Figure 10:
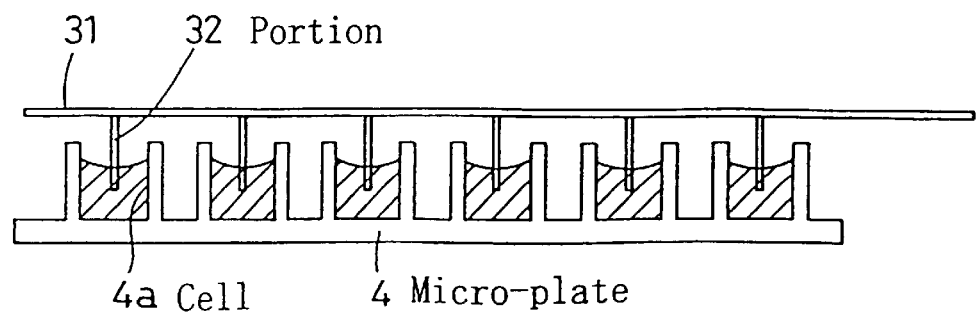
FIG. 10 is a central vertical cross-sectional view of the sensor illustrated in FIG. 9.

FIG. 9 is a plan view of a sensor of yet another embodiment according to the present invention, while FIG. 10 is a central vertical cross-sectional view thereof.

This sensor is arranged by forming cutout sections for pulling and standing at predetermined positions of an isolation substrate 31 which has a plan shape which is nearly equal to that of a micro-plate, and by forming active electrodes 33 and counter-electrodes 34 on each portion 32 which is permitted pulling and standing, each cutout section corresponding to each cell 4a of a micro-plate 4. And, lead-out terminals 35 are formed on one edge section of the isolation substrate 31. Also, wirings 36 for electrically connecting the active electrode 33 and counter-electrode 34 to the lead-out terminals 36 are formed on the isolation substrate board 31.

When this embodiment is employed, each electrode section is determined to be vertical with respect to the isolation substrate 31, as is illustrated in FIG. 10, by pulling and standing each portion 32. Under this condition, the isolation substrate 31 is moved so that each electrode section can be intruded into corresponding cell 4a. Further, all electrode sections are intruded into the cells almost simultaneously, so that dispersion in measurement data is greatly reduced. And, spatial limitation and limitation in dealing are determined to be nearly zero so that limitation in a number of objects which can be measured at one measurement operation is greatly lightened.

Further, in this embodiment, it is possible that a board curved in a wave-shape is employed as the isolation substrate 31 and that a portion which becomes a shape nearly following an inner face of the cell 4a when the portion is pulled and stood, is employed as the portion 32 which is permitted pulling and standing. When this modified example is employed, objects are easily supplied in each cell using a pipette for micro-plate or the like under a condition where the electrode sections are intruded into all cells 4a of the micro-plate 4. Further, operations and effects are realized which are similar to those of the above embodiment.

Figure 11:
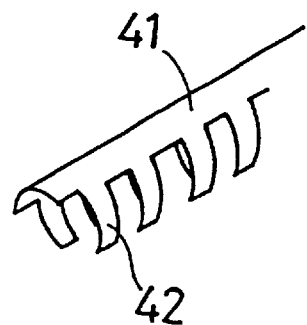
FIG. 11 is a perspective view illustrating a sensor of a yet further embodiment according to the present invention.

FIG. 11 is a perspective view illustrating a sensor of a yet further embodiment according to the present invention.

This sensor is arranged by providing first projection sections 42 at both longer sides of an elongate base body 41 at every predetermined distance. Further, active electrodes (not illustrated), counter-electrodes (not illustrated), and reference electrodes (not illustrated) are formed on each first projection section 42, the reference electrodes being provided when they are needed. Furthermore, lead-out terminals (not illustrated) are formed at an edge section of the base body 41, and wirings for connecting the active electrodes, and the counter-electrodes to the lead-out terminals are formed on the base body 41.

When this embodiment is employed, the entire measurement labor is greatly reduced. Also, spatial limitation and limitation in handling are greatly reduced so that limitation in a number of objects which can be measured at one measurement operation is lightened. Further, contacting condition of all electrode sections and objects, temperature circumstance, and connecting condition of all lead-out terminals and the connector are determined to be nearly equal to one another so that dispersion in measurement data is greatly reduced.

Figure 12:
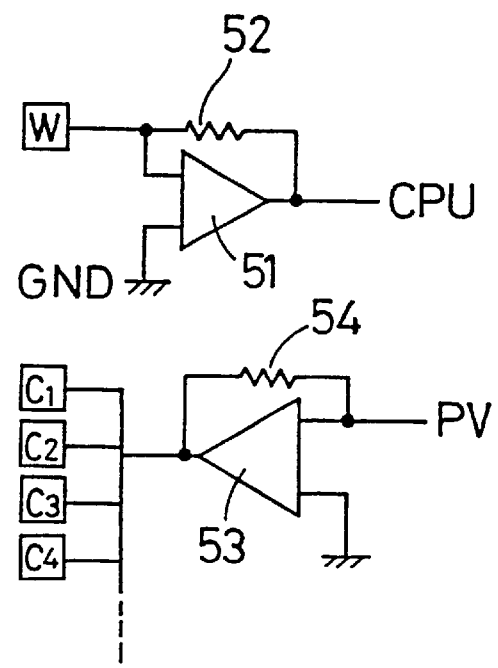
FIG. 12 is an electrical circuit diagram illustrating an electrical arrangement of an amplifier.

FIG. 12 is an electric circuit diagram illustrating an electric arrangement of an amplifier 7 of an example. This amplifier 7 corresponds to an electrode section which consists an active electrode and a counter-electrode. Further, in FIG. 12, the active electrode is represented with "W", while the counter-electrode is represented with "C".

In this amplifier 7, an output signal from the active electrode is supplied to a non-reverse input terminal of an operational amplifier 51, a reverse input terminal of the operational amplifier 51 is connected to the ground GND, a resistor 52 is connected between the non-reverse input terminal and an output terminal of the operational amplifier 51, and an output signal from the output terminal is output as an amplified signal. Further, a bias voltage is applied to a non-reverse input terminal of an operational amplifier 53, a reverse input terminal of the operational amplifier 53 is connected to the ground GND, a resistor 54 is connected between the non-reverse input terminal and an output terminal of the operational amplifier 53, and an output voltage from the output terminal is applied to the counter-electrode.

Therefore, the bias voltage is applied to the counter-electrode through the operational amplifier 53. Under this condition, the measurement signal output from the active electrode is amplified by the operational amplifier 51, and the amplified measurement signal is output from the operational amplifier 51.

Figure 13:
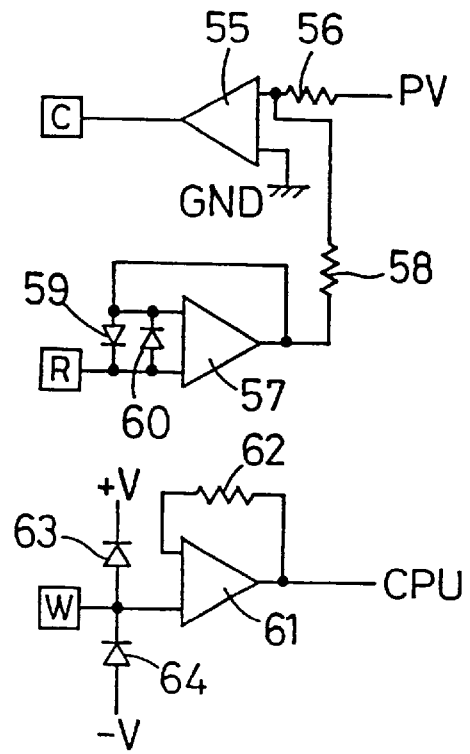
FIG. 13 is an electrical circuit diagram illustrating another electrical arrangement of an amplifier.

FIG. 13 is an electric circuit diagram illustrating an electric arrangement of an amplifier 7 of another example. This amplifier 7 corresponds to an electrode section which consists an active electrode, a counter-electrode and a reference electrode. Further, in FIG. 13, the active electrode is represented with "W", the counter-electrode is represented with "C", and the reference electrode is represented with "R".

In this amplifier 7, a bias voltage is applied to a non-reverse input terminal of an operational amplifier 55 through a resistor 56, a reverse input terminal of the operational amplifier 55 is connected to the ground GND, and an output voltage output from an output terminal of the operational amplifier 55 is applied to the counter-electrode. Further, an output signal from the reference electrode is supplied to a reverse input terminal of an operational amplifier 57, a non-reverse input terminal and an output terminal of the operational amplifier 57 are connected with short circuit (directly) to one another, and an output voltage from the output terminal is applied to the non-reverse input terminal of the operational amplifier 55 through a resistor 58. Furthermore, diodes 59 and 60 are connected in parallel and in reverse polarity to one another between the non-reverse input terminal and the reverse input terminal of the operational amplifier 57. Further, an output signal from the active electrode is supplied to a reverse input terminal of an operational amplifier 61, a resistor 62 is connected between a non-reverse input terminal and an output terminal of the operational amplifier 61, and an output signal from the output terminal is output as an amplified signal. Furthermore, a predetermined positive voltage and a predetermined negative voltage are applied to the non-reverse input terminal of the operational amplifier 61 through diodes 63 and 64, each being connected in reverse polarity, for performing a counterplan for a case where noises or the like are added to the output signal which is supplied to the non-reverse input terminal of the operational amplifier 61, or the like.

Therefore, the bias voltage with respect to the reference electrode is applied to the counter-electrode through the operational amplifiers 55 and 57. A measurement signal output from the active electrode under this condition is amplified by the operational amplifier 61, and the amplified measurement signal is output therefrom.

Figure 14:
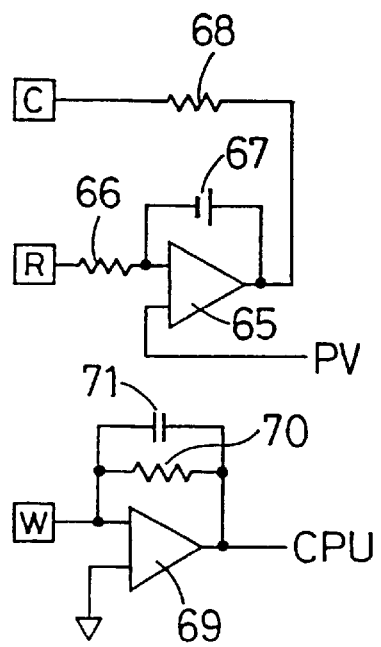
FIG. 14 is an electrical circuit diagram illustrating a further electrical arrangement of an amplifier.

FIG. 14 is an electric circuit diagram illustrating an electric arrangement of an amplifier 7 of a further example. This amplifier 7 corresponds to an electrode section which consists an active electrode, a counter-electrode and a reference electrode. Further, in FIG. 14, the active electrode is represented with "W", the counter-electrode is represented with "C", and the reference electrode is represented with "R".

In this amplifier 7, an output signal from the reference electrode is supplied to a non-reverse input terminal of an operational amplifier 65 through a resistor 66, a bias voltage is applied to a reverse input terminal of the operational amplifier 65, a capacitor 67 is connected between the non-reverse input terminal and an output terminal of the operational amplifier 65, and an output voltage from the output terminal of the operational amplifier 65 is applied to the counter-electrode through a resistor 68. Further, an output signal from the active electrode is supplied to a non-reverse input terminal of an operational amplifier 69, a resistor 70 and a capacitor 71 are connected in parallel to one another between the non-reverse input terminal and an output terminal of the operational amplifier 69, and an output signal from the output terminal is output as an amplified signal. Furthermore, a reverse input terminal of the operational amplifier 69 is connected to an adequate bias.

Therefore, a bias voltage with respect to the reference electrode is applied to the counter-electrode through the operational amplifier 65. A measurement signal output from the active electrode under this condition is amplified by the operational amplifier 69, and the amplified measurement signal is output therefrom.

Figure 15:
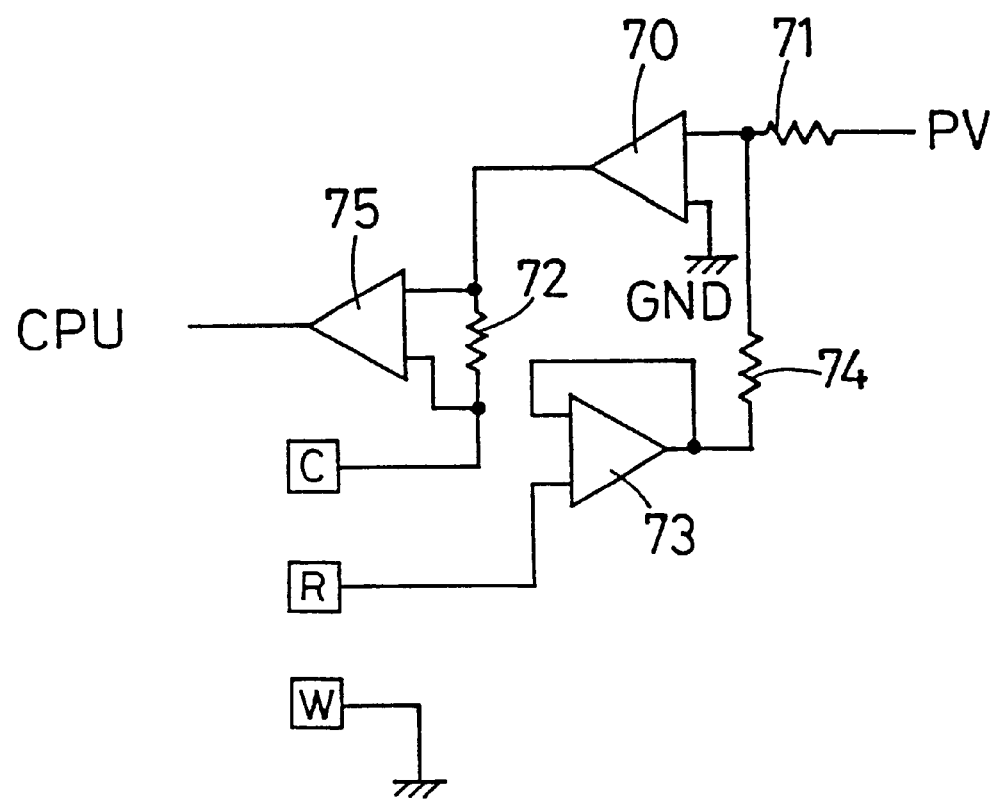
FIG. 15 is an electrical circuit diagram illustrating a yet electrical arrangement of an amplifier.

FIG. 15 is an electric circuit diagram illustrating an electric arrangement of an amplifier 7 of a yet further example. This amplifier 7 corresponds to an electrode section which consists an active electrode, a counter-electrode and a reference electrode. Further, in FIG. 15, the active electrode is represented with "W", the counter-electrode is represented with "C", and the reference electrode is represented with "R".

In this amplifier 7, a bias voltage is applied to a non-reverse input terminal of an operational amplifier 76 through a resistor 77, a reverse input terminal of the operational amplifier 76 is connected to the ground GND, and an output voltage from an output terminal of the operational amplifier 76 is applied to the counter-electrode through a resistor 72. Further, an output signal from the reference electrode is supplied to a reverse input terminal of an operational amplifier 73, a non-reverse input terminal and an output terminal of the operational amplifier 73 are connected with short circuit (directly) to one another, and an output voltage from the output terminal of the operational amplifier 73 is applied to a non-reverse input terminal of an operational amplifier 76 through a resistor 74. Furthermore, an output signal from the active electrode is supplied to the ground GND, voltages at both ends of the resistor 72 are applied to a reverse input terminal and a non-reverse input terminal of an operational amplifier 75, and an output signal from an output terminal of the operational amplifier 75 is output as an amplified signal.

Therefore, the bias voltage with respect to the reference electrode is applied to the counter-electrode through the operational amplifiers 73 and 76. And, a measurement signal output from the active electrode under this condition is amplified by the operational amplifiers 75 and 76, and the amplified signal is output therefrom.

Figure 16:
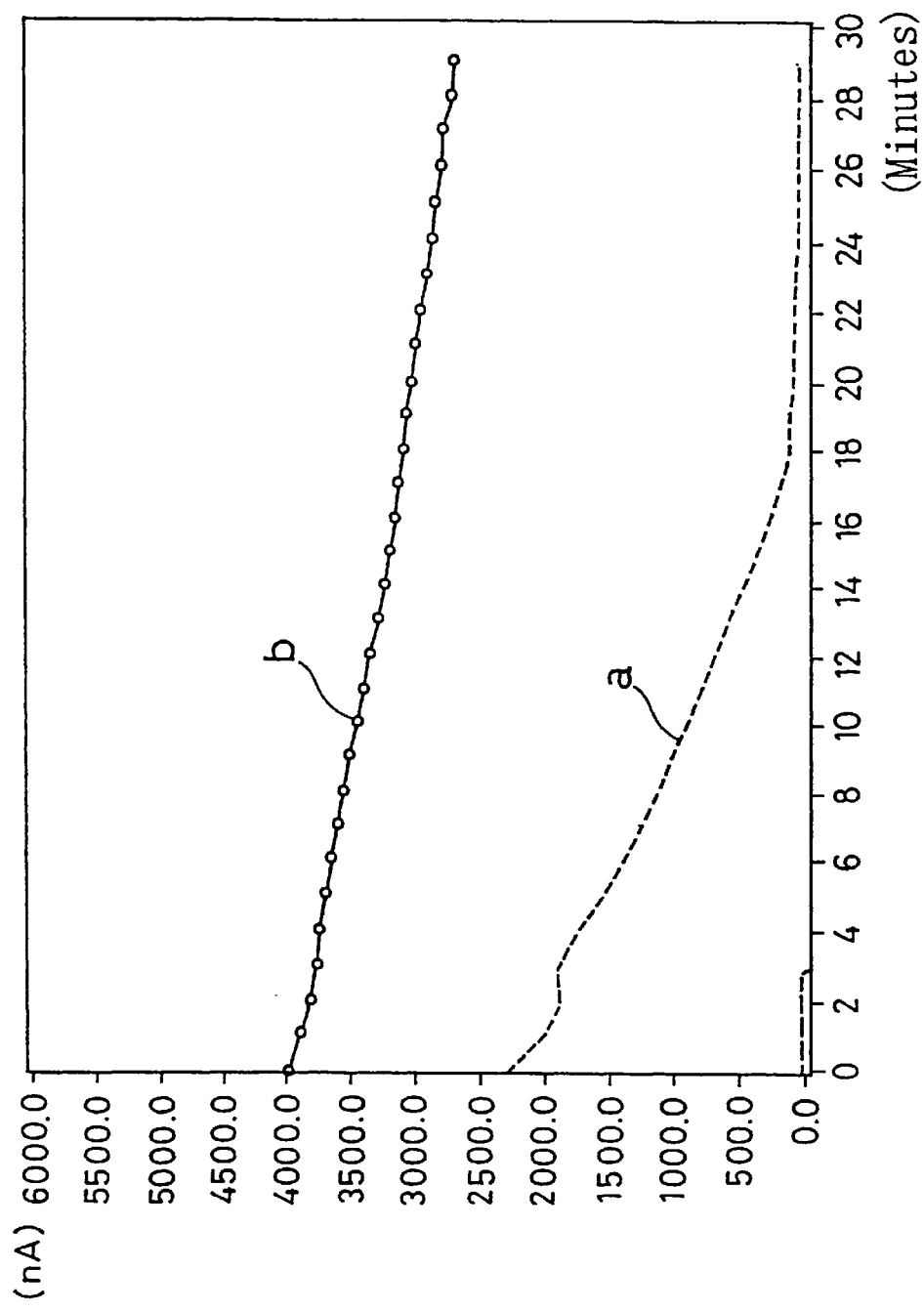
FIG. 16 is a diagram illustrating a measurement results representing changes in dissolved oxygen amount within an object which is made of only culture medium and within an object which is made by adding colibacillus (*E. coli*) of final concentration of $5 \times 10^6$/ml to culture medium, the dissolved oxygen amount being measured using a partial electrode sections of the sensor illustrated in FIG. 1.

FIG. 16 is a diagram illustrating a measurement results representing changes in dissolved oxygen amount within an object which is made of only culture medium and within an object which is made by adding colibacillus (E. coli) of final concentration of 5×10⁶/ml to culture medium, the dissolved oxygen amount being measured using a partial electrode sections of the sensor illustrated in FIG. 1. Further, the horizontal axis represents a time (minutes), while the vertical axis represents a detection current (nA). Furthermore, "a" represents the former case, while "b" represents the latter case.

As is apparent from FIG. 16, it is understood that the dissolved oxygen amount is decreased due to respiration of colibacillus when colibacillus is added. It is also understood that the dissolved oxygen amount can be measured using the sensor according to the present invention. Further, the dissolved oxygen amount within the object which is made of only culture medium, is gradually decreased. It is thought that the gradual decreasing of the dissolved oxygen amount represents decreasing of the dissolved oxygen amount due to the affection of the electrode section.

Figure 18:
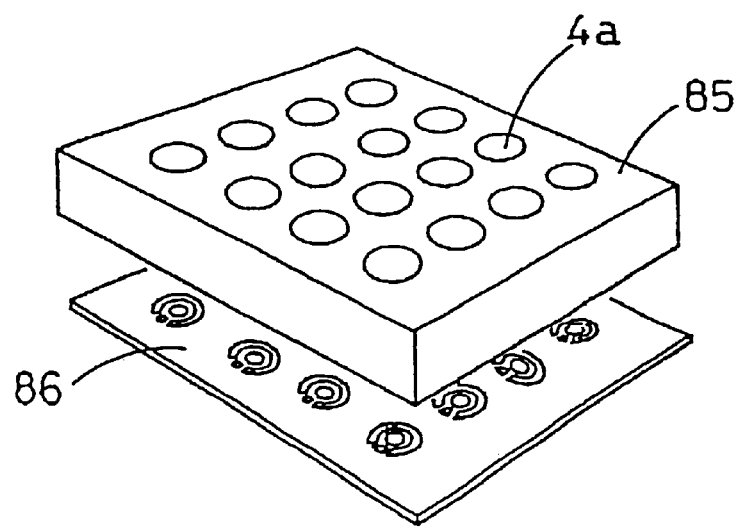
FIG. 18 is a deal perspective view illustrating a sensor of a further embodiment according to the present invention.
Figure 19:
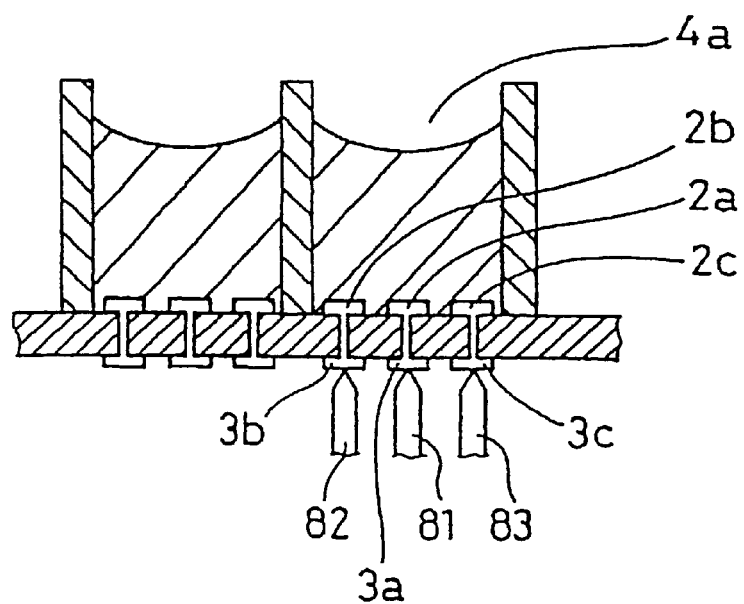
FIG. 19 is an enlarged vertical cross-sectional view of a main section of the sensor illustrated in FIG. 18.
Figure 20:
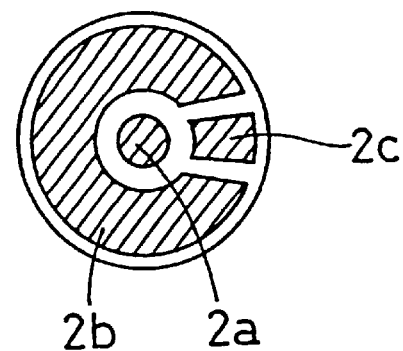
FIG. 20 is a plan view of FIG. 19.

FIG. 18 is a deal perspective view illustrating a sensor of a further embodiment according to the present invention. FIG. 19 is an enlarged vertical cross-sectional view of a main section of the sensor illustrated in FIG. 18. FIG. 20 is a plan view of FIG. 19.

This sensor is arranged by disposing an upper plate 85 on a bottom plate 86, the upper plate 85 having a plurality of column shape through holes, by uniting the both plates in one body in a watertight manner so that a plurality of object housing chambers 4a is constructed. Further, Active electrodes 2a are formed at upper central sections of portions of the bottom plate 86, each portion corresponding to bottom wall section of each object housing chamber 4a, and counter-electrodes 2b and reference electrodes 2c are formed so that each counter-electrode 2b and corresponding reference electrode 2c are disposed so as to realize ring shapes, the center of the ring shape is determined to be the active electrode 2a. Furthermore, sizes of the counter-electrode 2b and the reference electrode 2c are determined so that the former size is greater than the latter size. Further, the active electrode 2a, the counter-electrode 2b and the reference electrode 2c consist an electrode section.

Further, lead-out terminals 3a, 3b and 3c are formed on a lower face of a portion of the bottom plate 86. The portion corresponds to the bottom wall section of the object housing chamber 4a, and the lead-out terminals 3a, 3b and 3c correspond to the active electrode 2a, the counter-electrode 2b and the reference electrode 2c. And, connection sections (for example, through sections each made of silver paste) are formed for electrically connecting the active electrode 2a and the lead-out terminal 3a, the counter-electrode 2b and the lead-out terminal 3b, and the reference electrode 2c and the lead-out terminal 3c, respectively. Furthermore, contactors 81, 82 and 83 are illustrated in FIG. 19 which are electrically contacted to the lead-out terminals 3a, 3b and 3c.

When the sensor having this arrangement is employed, measurement of a plurality of objects is carried out simultaneously by pouring objects into the object housing chambers 4a, and by electrically contacting the contactors 81, 82 and 83 to the lead-out terminals 3a, 3b and 3c. Further, though the electrode section is provided to the object housing chamber 4a in one body, spatial limitation and limitation in handling are greatly reduced and limitation in a number of objects which can be measured at one measurement operation is lightened. Furthermore, contacting condition of all electrode sections and objects, temperature circumstance, and connecting condition of all lead-out terminals and the contactors are determined to be nearly equal to one another so that dispersion in measurement data is greatly reduced.

Figure 21:
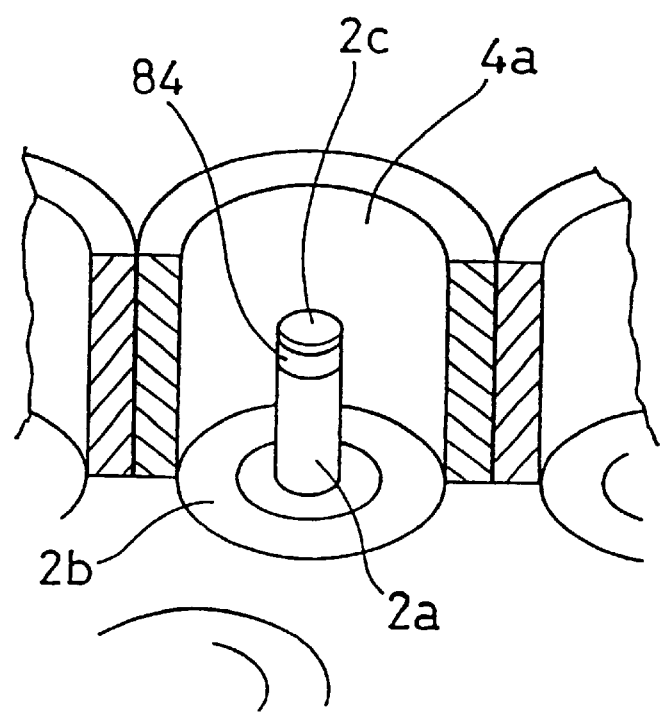
FIG. 21 is a perspective view of a portion of a sensor of a further embodiment according to the present invention, the view illustrating a main section in a cut away manner.
Figure 22:
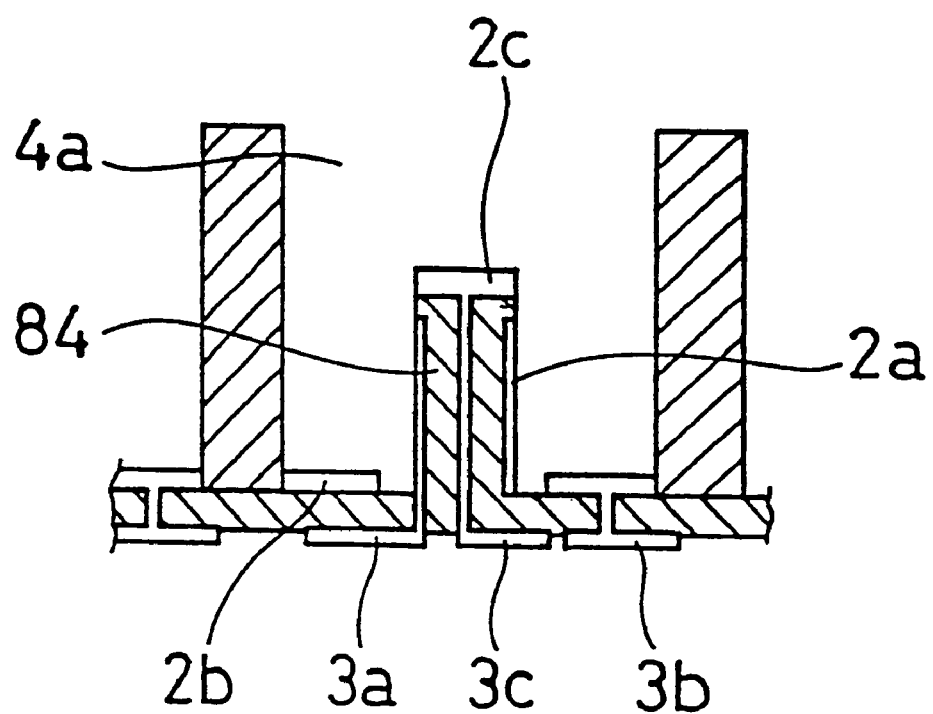
FIG. 22 is a vertical cross-sectional view of the sensor illustrated in FIG. 21.

FIG. 21 is a perspective view of a portion of a sensor of a further embodiment according to the present invention, the view illustrating a main section in a cut away manner, while FIG. 22 is a vertical cross-sectional view thereof.

This sensor is different from the above sensor in that axial sections 84 are provided each elongates upwards from a central section of an upper face of a portion of the bottom plate which portion corresponds to the bottom wall section of the object housing chamber 4a, and that the reference electrode 2c is formed on an upper face of the axial section 84, the active electrode 2a is formed on a side face of the axial section 84, and the counter-electrode 2b is formed on the upper face of the portion of the bottom plate which portion corresponds to the bottom wall section of the object housing chamber 4a, the counter-electrode 2a being coaxial to the axial section 84.

When this embodiment is employed, areas of the active electrode 2a and the counter-electrode 2b can be enlarged without increasing the inner diameter of the object housing chamber 4a. Further, operations and effects are realized which are similar to those of the above embodiment.

INDUSTRIAL APPLICABILITY

The sensor according to the present invention is available for a sensor which measures objects using a micro-plate having object housing chambers of multiple lines and multiple columns. And, measurement labor is greatly reduced, dispersion in measurement data is greatly reduced, and limitation in a number of objects which can be measured at one measurement operation is lightened.

What is claimed is:

1. A sensor for sensing cells in a micro-plate wherein the cells are spaced from each other by a predetermined distance, said sensor comprising;

a base body having a plate shape;

projection sections provided along an outer portion of the base body, the projection sections being spaced apart from each other by the predetermined distance;

each projection section including at least an active electrode and a counter-electrode provided at a predetermined position on each projection section, each active electrode and each counter-electrode determining an electrode section; and multiple lead-out terminals for outputting measurement signals from each electrode section, each lead-out terminal being provided at a portion of the base body which opposes the portion along which the projection sections are provided.

2. A sensor as set forth in claim 1, further comprising;

a connector which is connected to the lead-out terminals in a removable manner; and an amplifier which amplifies the measurement signals output through the lead-out terminals;

and wherein the connector and the amplifier are united in one body.

3. A sensor as set forth in claim 2, wherein the connector is a connector which connects multiple base bodies in parallel to one another and in a removable manner, and the amplifier is an amplifier which amplifies measurement signals, respectively, each measurement signal being output through the corresponding lead-out terminal.

4. A sensor comprising;

a substrate defining multiple object housing chambers;

an electrode section located at a bottom section of each object housing chamber, each electrode section having at least an active electrode and a counter-electrode is formed at a bottom section of each object housing chamber; and multiple lead-out terminals (3a) for outputting measurement signals from each electrode section;

wherein the lead-out terminals are united with the object housing chambers.

5. A sensor comprising;

a base body having a plate shape and formed by a micro-plate or substrate;

projections sections of multiple lines and multiple columns, each projection section projecting by a predetermined angle from one surface of the base body;

electrode sections each including at least an active electrode and a counter-electrode which electrode section is provided at a predetermined position of each projection section; and multiple lead-out terminals for outputting measurement signals from each electrode section, which lead-out terminals are provided at predetermined positions on an edge section of the base body.

6. A sensor comprising;

multiple object housing chambers formed on a micro-plate or substrate;

electrode sections each having at least an active electrode and a counter-electrode, and each electrode section being formed on a bottom inner face of each object housing chamber; and multiple lead-out terminals for outputting measurement signals from each electrode section, each lead-out terminal being provided so that the lead-out terminal is exposed at an outer face of a bottom section of each object housing chamber.

7. A sensor comprising;

multiple object housing chambers;

inner projections each projecting to an inner side from a center section of an inner face of an edge section of each object housing chamber;

electrode sections each having at least an active electrode and a counter-electrode, each electrode section being formed at a predetermined position of an outer face of the inner projection and/or the inner face of the edge section; and multiple lead-out terminals for outputting measurement signals from each electrode section, each lead-out terminal being provided so that the lead-out terminal is exposed at an outer face of a bottom section of each object housing chamber.

8. A sensor as set forth in claim 7, wherein the inner projection is an axial section which extends upward from a central section of the bottom inner face of each object housing chamber, and the electrode section includes an active electrode on an outer face of the axial section and a counter-electrode on an upper face of the bottom section of each object housing chamber.

* * * * *